United States Patent [19]

Miyake et al.

[11] Patent Number: 5,174,162
[45] Date of Patent: Dec. 29, 1992

[54] PIPETTER, PIPETTE TUBE, SAMPLE ANALYZING APPARATUS INCLUDING THEM AND METHOD OF MIXING AND PIPETTING LIQUIDS

[75] Inventors: Ryo Miyake, Shimoinayoshi; Hiroshi Ohki, Tsuchiura; Hideo Enoki, Shimoinayoshi; Toshio Kaneko, Katsuta; Hideyuki Horiuchi, Abiko, all of Japan

[73] Assignee: Hitachi, Ltd., Tokyo, Japan

[21] Appl. No.: 550,543

[22] Filed: Jul. 10, 1990

[30] Foreign Application Priority Data

Jul. 10, 1989 [JP] Japan .................. 1-175494

[51] Int. Cl.⁵ ............... B01L 3/02; G01N 1/14
[52] U.S. Cl. .................. 73/864.21; 73/864.22; 73/864.11; 73/863.32; 250/437; 250/438
[58] Field of Search ........... 73/864.21, 864.11, 864.22, 73/863.32, 864.24, 864.25, 864.01, 864.14, 863.43, 863.41; 436/174, 165; 250/451, 438

[56] References Cited

U.S. PATENT DOCUMENTS

| | | | |
|---|---|---|---|
| 1,547,562 | 7/1925 | Byrd | 73/864.01 X |
| 1,762,807 | 6/1930 | Arnold | 73/864.01 |
| 2,104,325 | 1/1938 | Juffa | 73/864.01 X |
| 2,322,018 | 6/1943 | Huber | 73/863.43 X |
| 2,398,737 | 4/1946 | Elliot et al. | 73/864.01 X |
| 2,836,979 | 6/1958 | Ryley | 73/864.01 |
| 4,022,575 | 5/1977 | Hansen et al. | 436/150 X |
| 4,117,728 | 10/1978 | Johnson | 73/864.18 |
| 4,403,517 | 9/1983 | Thomte | 73/864.43 X |
| 4,494,413 | 1/1985 | Bukkems et al. | 73/864.43 |
| 4,841,786 | 6/1989 | Schulz | 73/864.25 |
| 4,902,629 | 2/1990 | Meserol et al. | 436/165 |
| 5,051,238 | 9/1991 | Umetsu et al. | 422/67 X |
| 5,079,959 | 1/1992 | Miyoke et al. | 73/864.22 X |

FOREIGN PATENT DOCUMENTS

| | | | |
|---|---|---|---|
| 105834 | 4/1984 | European Pat. Off. | 73/864.01 |
| 0107333 | 5/1984 | European Pat. Off. | |
| 286088 | 10/1988 | European Pat. Off. | |
| 0336309 | 10/1989 | European Pat. Off. | |
| 360487 | 3/1990 | European Pat. Off. | 73/864.21 |
| 859538 | 1/1952 | Fed. Rep. of Germany | 73/864.01 |
| 3839080 | 6/1989 | Fed. Rep. of Germany | |
| 9585 | 3/1986 | Japan | 73/864.22 |
| 744269 | 6/1980 | U.S.S.R. | 73/864.11 |
| 866529 | 4/1961 | United Kingdom | 73/864.01 |

OTHER PUBLICATIONS

*Patent Abstracts of Japan*, Grp. P1050, vol. 14, No. 238, Abs. Pub. Date May 21, 1990 (02-59670).
*Patent Abstract of Japan*, Grp. P924, vol. 13, No. 387, Abs. Pub. Date Aug. 21, 1989 (01-136008).

*Primary Examiner*—Tom Noland
*Attorney, Agent, or Firm*—Antonelli, Terry, Stout & Kraus

[57] ABSTRACT

A pipetter capable of mixing liquids and dispensing the mixed liquid has a pipetting tube, an actuating device connected to the tube for sucking liquid into and discharging liquid from the tube, and a flow disturbance device in the tube spaced from the discharge and suction end thereof and adapted to cause longitudinal mixing of liquid in the tube when liquid is moved along the tube in at least one direction. Mixing is effected in the tube by causing a liquid body to move repeatedly to and fro along the tube so that during each such movement at least a portion of the liquid body passes the flow disturbance device and the liquid body is not discharged from the first end of the tube. The pipetter is useful for example in mixing a suspension of blood cells with a reagent prior to analysis.

12 Claims, 7 Drawing Sheets

PIPETTER, PIPETTE TUBE, SAMPLE ANALYZING APPARATUS INCLUDING THEM AND METHOD OF MIXING AND PIPETTING LIQUIDS

BACKGROUND OF THE INVENTION

1. Field of the Invention

This invention relates to pipetters and pipette tubes. It also relates to sample analyzing apparatus, especially particle analyzing apparatus including such pipetters and pipette tubes, and to a method of simultaneously mixing and pipetting liquids. While not limited thereto, the invention is especially applicable in the medical field to the analysis of blood cells which are suspended in a solution.

2. Description of the Prior Art

In many fields, a sample liquid has to be mixed with a reagent liquid prior to analysis. The reagent liquid may only have the function of diluting the sample liquid, or it may react with the sample liquid or particles suspended in the sample liquid. An example, to which the invention is applicable, is the preparation of blood cells for flow cytometry, e.g. red cells, white cells, reticulocytes (young blood cells) or lymphocytes, in which a suspension of cells in a liquid is reacted with a reagent which dyes the cells. Subsequently the dyed cells are passed through a flow cell, in which they are counted or are qualitatively analysed using a light beam.

A convenient technique for transferring small predetermined quantities of liquids is pipetting. Conventionally the steps of mixing two liquids and of pipetting a predetermined amount of the mixture have been performed separately. However, apparatus can be simplified and processing time reduced by combining these steps. The present invention is concerned with achieving such a combination satisfactorily.

A method of processing a sample by use of a pipetter is described in Japanese Patent Publication No. 9585/1986 (JP-B-86-9585). This reference relates to a dilution method which dilutes and dispenses a sample by use of a pipette tube including a mixing chamber which has a sectional area greater than the sectional area of the sample dispensing nozzle of the tube. This method comprises a first step of sucking a predetermined amount of the sample into the pipette tube from a sample vessel using a diluting solution as the pipette operating liquid, a second step of introducing the sucked sample inside the tube once into the mixing chamber when the nozzle of the tube is separated from the sample vessel and thereby partially mixing the diluting solution with the sample, and a third step of discharging the partially mixed sample into a vessel in which further mixing of the sample and the diluting fluid take place.

In the prior art method described above, mixing efficiency is low because the sample is merely introduced into the mixing chamber having an expanded sectional area. This method also employs the method of feeding a large quantity of washing water or the diluting solution from the upper part of the pipette tube at the time of washing of the tube, but if the washing solution is merely passed into the mixing chamber, an eddy occurs in the flow at the expanded portion and residual sample may be left, so that contamination is likely to occur. In other words, there is a problem that "carry-over" is likely to develop in which trace amounts of one sample contaminate the next.

SUMMARY OF THE INVENTION

It is an object of the present invention to provide apparatus and method for mixing and pipetting which provides a uniform mixing concentration, has high reaction and mixing efficiency and can make washing easy.

It is another object of the present invention to provide a sample analyzing apparatus which, though simple in construction, can effect efficient mixing of a liquid with a reagent solution and accurate dispensing of the mixture to an analysis device.

According to the invention in one aspect, there is provided a pipetter capable of mixing liquids, having a pipetting tube having a first end for suction and discharge of liquid being pipetted and a second end, and actuating means connected to said second end of said tube for sucking liquid into and discharging liquid from said tube via said first end. Flow disturbance means are arranged in said tube spaced from said first end and adapted to cause longitudinal mixing of liquid in said tube when liquid is moved along said tube past said flow disturbance means in at least one direction. There are control means for said actuating means adapted and arranged to effect mixing in said tube by causing said actuating means to move a liquid body repeatedly to and fro along said tube so that during each such movement at least a portion of said liquid body passes said flow disturbance means and said liquid body is not discharged from said first end of said tube. Preferably said control means is programmable and is programmed to cause said actuating means to effect said mixing.

Longitudinal mixing is mixing of liquid portions initially spaced from each other along the tube, as initially is the case when two liquids are sucked sequentially into a pipette tube.

A particular advantage of the invention is that thorough mixing can be achieved in the pipetter, removing the need for subsequent mixing of the liquids and allowing immediate accurate dispensing of the desired quantity of mixture.

Another advantage, for certain liquids containing suspended solid particles, such as blood cells, is that use of a moving mechanical stirrer can be avoided. The flow disturbance means in the pipetter is typically a static device, producing only vortices or turbulence in the liquid. This is less likely to damage the cells than a moving stirrer.

A preferred form of said flow disturbance means is a mixing chamber having a lower end of a cross-sectional shape providing a sharp transition causing turbulent flow of liquid on entry into said chamber in the flow direction away from said first end of said tube. Other suitable forms of flow disturbance means are (a) a plurality of vanes causing swirling of the liquid,
(b) at least one element extending across the liquid flow path and causing eddying of the liquid,
(c) a plurality of bends, preferably reverse bends, providing a serpentine region of the liquid flow path, and
(d) a wider liquid flow path region adjoining narrower liquid flow path regions wherein the liquid flow direction changes at the junction of at least one of said narrower flow path regions to said wider flow path region.

In another aspect, the invention provides a pipette tube having a first end for suction and discharge of liquid being pipetted, and a second end for attachment to actuating means for causing sucking and discharge of liquid being pipetted via said first end. A liquid mixing chamber is arranged in said tube remote from said ends, and a first portion of said tube of narrower cross-sectional area than said mixing chamber extends away from said mixing chamber towards said first end, while a second portion of said tube of narrower cross-sectional area than said mixing chamber extends away from said mixing chamber towards said second end. The mixing chamber has a cross-sectional shape such that there are:
(i) a widest region closer to said first portion than to said second portion,
(ii) a sharp transition from said first portion into said mixing chamber so that liquid flowing from said first portion tends to have turbulent flow, and
(iii) a gradually tapering region extending from said widest region to said second portion.

In another aspect, the invention consists in a particle analyzer for analyzing suspended particles in a liquid sample, comprising at least one sample container for said sample, at least one container for a second liquid to be mixed with said sample prior to analysis thereof, and a sensor for analyzing particles in said sample after mixing with said second liquid. The analyzer has a pipetter according to the invention as described above adapted and arranged for sucking a predetermined quantity of said sample from said sample container, mixing said sample with said second liquid to form a mixture thereof and discharging at least part of said mixture to said sensor.

For the analysis for example of blood cells or other particles, the particle analyzer preferably has a sensor which is a sheath flow cell connectable to the pipette tube for introduction of the mixture into said sheath flow cell, the sensor including means for irradiating the particles in said sheath flow cell and means for detecting radiation resulting from irradiation of said particles by said irradiating means.

In another aspect the invention provides sample analyzing apparatus capable of simultaneous handling of a plurality of samples, comprising a plurality of sample containers for said samples, at least one sensor for said samples, and a plurality of pipetters adapted and arranged for sucking said samples from said sample containers, forming mixtures of said samples with a second liquid and discharging said mixtures to said at least one sensor, each said pipetter being a pipetter of the invention as described above.

The invention can provide sample analyzers of simple construction. The use of a pipette or pipettes avoids long tubing which is difficult to clean, and allows very small sample volumes to be accurately transferred. A high efficiency of mixing can be achieved in a short time. Washing is easy, so that risk of contamination by "carry-over" is low or is avoided entirely. The space occupied by the pipetting apparatus is relatively small. The volume of washing solution required is low.

In its method aspect, the invention provides a method of mixing and pipetting liquids, comprising the steps of:
(a) arranging two different liquids which are to be mixed adjacent each other in a pipette tube, by sucking a predetermined amount of at least one of said liquids into said pipette tube,
(b) repeatedly effecting movement of said two liquids to and fro along said pipette tube so that in each said movement they at least partly pass flow disturbance means in said tube, thereby effecting longitudinal mixing of said two liquids in the tube, while retaining said liquids in said tube,
(c) discharging a predetermined amount of the mixed liquids from said pipette tube.

The minimum number of the to and fro movements is two, i.e. at least part of the liquids being mixed pass the flow disturbing means at least twice in the same direction. Preferably at least four of said to and fro movements are performed, and more preferably the number of such to and fro movements is in the range of 6 to 20.

When the movements of the liquids being mixed are caused by movement of a pipette operating liquid, there is preferably a gas pocket maintained between said pipette operating liquid and the liquids being mixed.

The invention is especially applicable to the mixing of discrete small amounts of liquid, e.g. not more than 10 ml, typically less than 1 ml.

BRIEF INTRODUCTION OF THE DRAWINGS

Embodiments of the invention will now be described by way of non-limitative example, with reference to the accompanying drawings in which:

FIG. 12a is an exploded perspective view of another pipette tube embodying the invention;

FIG. 12b is a perspective view of the assembled pipette tube of FIG. 12a; and

DESCRIPTION OF THE PREFERRED EMBODIMENTS

Figure 1:
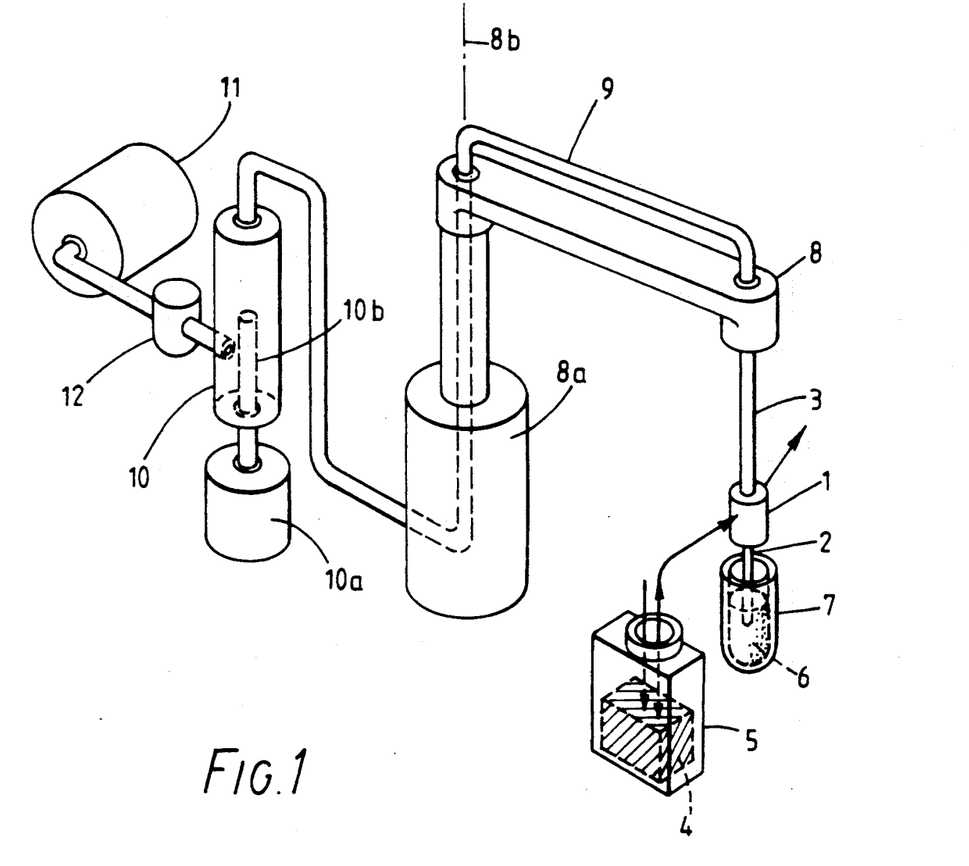
FIG. 1 is a general perspective view of parts of a pipetting and mixing apparatus embodying the invention.
Figure 2:
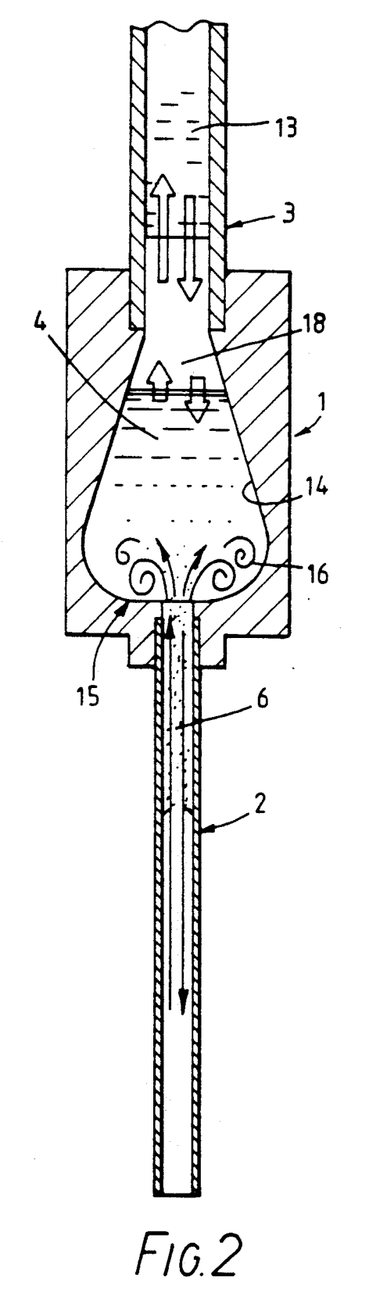
FIG. 2 is an enlarged sectional view of part of the pipette tube of the apparatus of FIG. 1.
Figure 13:
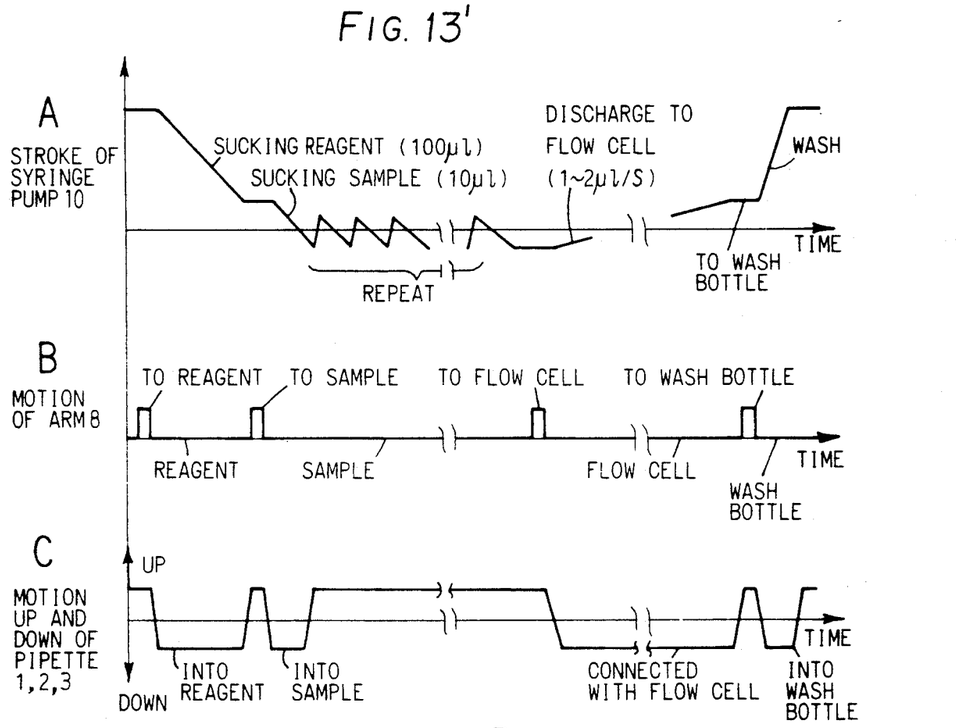
FIGS. 13 and 13' (hereafter referred to collectively as FIG. 13) together form an operational diagram illustrating the control of a sample analyzer embodying the invention.

FIGS. 1 and 2 show a pipetter embodying the invention and used in the particle analyzer whose operation is illustrated in FIG. 13. The pipetter has a pipette tube having a lower tube portion 2 ending at its lower end in an open suction and discharge mouth, a mixing chamber 1 and an upper tube portion 3.

The upper tube portion 3 and a syringe pump 10 are connected by a tube 9 carried by a swinging arm 8 which is rotated around the vertical axis 8b and moved up and down by a drive means diagrammatically shown at 8a. The sucking and discharging operation of the syringe pump 10 is under the action of a drive means 10a which moves a piston 10b of the pump up and down. This movement is transmitted to the pipette tube 1,2,3 by a dispensing operation solution 13 filling the tube 9. The syringe pump 10 and a solution feed pump 11 are connected by a tube through a solenoid valve 12.

A reagent tank 5 holding reagent 4 and a sample holding vessel 7 holding a sample, e.g. a particle suspension 6, are disposed below the rotation path of the lower tube portion 2. FIG. 2 shows that the mixing chamber 1 has an interior shape so as to provide a sharply increased diameter at location 15 at the junction with the lower tube portion 2 and to provide a gradually tapering shape 14 towards the junction with the upper tube portion 3.

The following operation is carried out by the pipetter described above.

First, the pipetter sucks a predetermined volume of air 18, starting from the state where the dispensing operation solution 13 is charged fully in the upper tube portion 3, the mixing chamber 1 and the lower tube portion 2. Next, the lower tube portion 2 is immersed into the reagent tank 5 and a predetermined amount of the reagent 4 is sucked. The pipetter is then moved into the sample holding vessel 7 and sucks a predetermined amount of the particle suspension 6. All these sucking operations are effected by the pump 10. At this time the dispensing operation solution 13 exists in the upper tube portion 3 as shown in FIG. 2, the air volume 18 exists in succession to the former and the body of reagent solution 4 is charged fully into the mixing chamber 1. This is the state when the particle suspension 6 has been sucked into the lower tube portion 2. Next, sucking is made rapidly from this state until the lower end of the body of particle suspension 6 reaches exactly the upper end of the lower tube portion 2, i.e. the position immediately before the inlet of the mixing chamber 1. At this time eddies 16 are generated in the chamber 1 by the rapidly expanding flow at the sharp change of cross-sectional area as shown in FIG. 2, and the particle suspension 6 and the reagent solution 4 are partly mixed into a single liquid body. However, since the mixing concentration is not uniform after only one mixing, the body of mixture is again at least partly returned into the lower tube portion 2 and is sucked rapidly once again into the mixing chamber 1. This to and fro movement caused by the pump 10 is repeated several times so that the particle suspension 6 and the reagent solution 4 are sufficiently mixed and/or reacted, thereby providing a thoroughly mixed sample solution. Thereafter the pipetter tube is moved to the predetermined supply destination and discharges the sample solution, or a predetermined desired amount thereof, from the pipetter tube 1,2,3. After this discharge operation is completed, the solenoid valve 12 is opened and the washing solution supplied by the feed solution pump 11 washes the upper tube portion 3, the mixing chamber 1 and the lower tube portion 2 through the syringe pump 10 and the tube 9.

The mixing chamber 1 has a progressively diminishing cross-sectional shape toward its upper end. The liquid flow inflowing from the upper tube portion 3 is thus progressively expanding. Therefore, eddies do not occur easily, so that the residues of the sample solution 17 are rapidly washed away.

The air volume 18 must be interposed between the dispensing operation solution 13 and the reagent solution 4. However, since the sectional area at the upper part of the mixing chamber 1 is smaller than that at its lower part, a relatively long distance can be obtained between the dispensing operation solution 13 and the reagent solution 4. Accordingly, the solution 12 and the reagent solution 4 are not mixed, and quantitative mixing of the sample with the reagent 6 is not lost. This effect can be attained with a small amount of air. If the air amount is great, the air may play the role of a spring or damper and the reagent solution and the particle suspension are not properly mixed. If the mixing chamber 1 shown in FIG. 2 is used, the air amount may be small and mixing of the operation solution 13 and the reagent solution can be prevented.

Next, other embodiments of the present invention will be explained.

Figure 3:
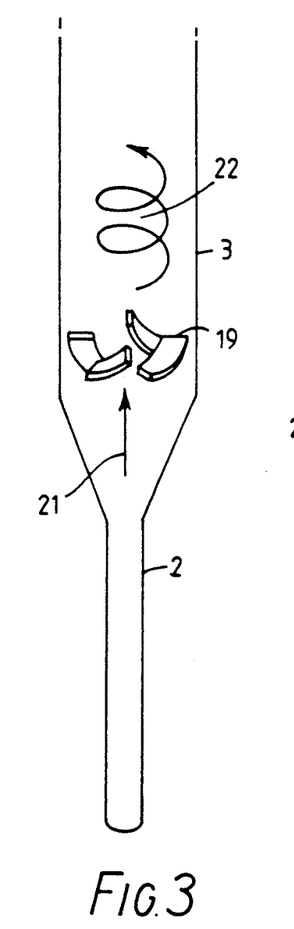
FIG. 3 is a perspective diagram of an alternative embodiment of the pipette tube of the apparatus of FIG. 1.
Figure 4:
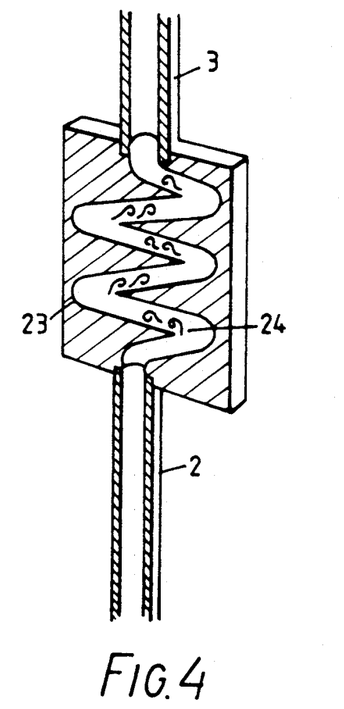
FIG. 4 is a cut-away perspective view of another alternative embodiment of the pipette tube of the apparatus of FIG. 1.
Figure 5:
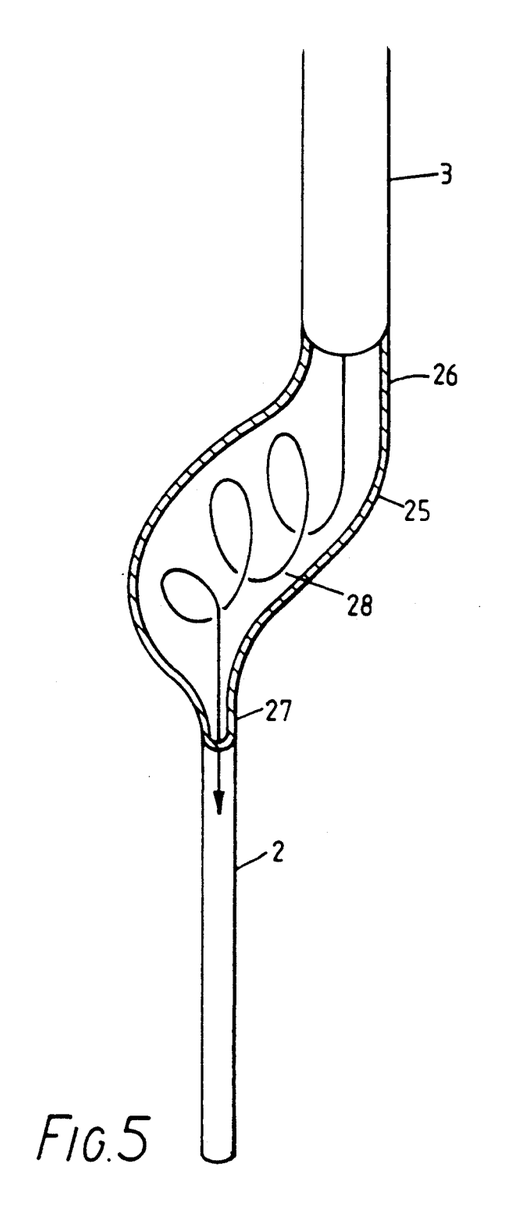
FIG. 5 is a cut-away perspective view of yet another alternative embodiment of the pipette tube of the apparatus of FIG. 1.

FIGS. 3, 4 and 5 show other embodiments of the pipette tube of the present invention. In FIG. 3, vanes 19 are fitted to the inner wall of the upper tube portion 3 and its operation is as follows. After the particle suspension and the reagent solution are sucked in respective predetermined amounts into the pipette tube, these solutions are united into a liquid body which is reciprocated to and fro past the vanes by the operation of the syringe pump 10. In this instance, a swirl flow 22 occurs in front of and behind the vanes 19 and promotes mixing and agitation.

In FIG. 4, the mixing chamber is a conduit with a plurality of bends 23 giving it a serpentine shape. An eddy flow indicated by reference numeral 24 occurs at each bend when a body of liquid composed of the particle suspension 6 and the reagent solution 4 are reciprocated through the bends. This promotes likewise mixing and agitation. It is advantageous that the bends 23 are acute (more than 90°) and that bends in several directions are adjacent.

Figure 6:
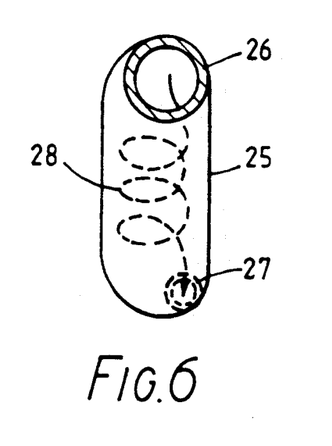
FIG. 6 is a section and top view of the tube of FIG. 5.

In the embodiment of the invention shown in FIG. 5, a wider bent tube portion 25 generating a spiral flow is disposed between the narrower upper tube portion 3 and the narrower lower tube portion 2. FIG. 6 is a top view showing that the connections 26,27 between the bent tube 25 and the upper and lower tube portions 2,3 are located at offset positions from the centre axial line of the tube 25 and at an angle to the general axial direction of the tube 25. Consequently the liquid flow direction changes at each of the connections 26,27. When the liquid reciprocates through the tube 25, spiral flow indicated by reference number 28 occurs and provides a mixing and agitation effect as well as the washing effect during the washing step.

Next, the particle analyzing apparatus using the pipetters similar to those of FIGS. 1 and 2 will be explained with reference to FIGS. 7 and 8. The apparatus is equipped with two such pipetters 29,30 that move up and down and traverse horizontally back and forth to reach the various storage and discharge locations, rather than rotating as in FIG. 1. An O-ring 31 is disposed on the outside near the tip of the lower tube portion 2 of each pipetter so as to ensure a seal at the time of connection of the pipette tube with a sheath flow cell 32. The two pipetters 29,30 are disposed in such a manner that when the respective pipette tubes move back and forth, their paths overlap with each other, and the sheath flow cell 32, a dispensing solution washing tank 34, the reagent tank 5 and the sample vessel 7 from which sample liquid is sucked are disposed in the order given below the path. A plurality of the sample vessels 7 are moved in a direction represented by arrow 33, each one containing a new sample for measurement. A laser source 35 and a laser beam condensing lens system 36 are disposed facing the sheath flow cell 32 and a lens system 37 for condensing scattered beam and/or fluorescence from the analyzed particles in the cell 32 and an optical detector 38 are disposed on the opposite side. The principles of construction and operation of the sheath flow cell 32 are known, e.g. from EP-A-360487.

Figure 7:
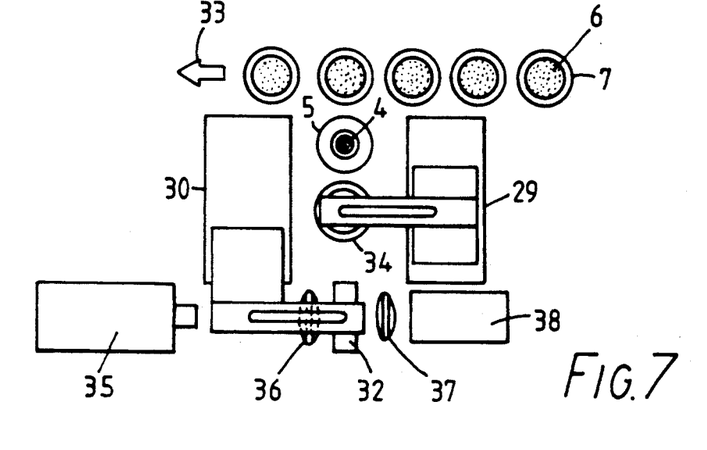
FIG. 7 is a general diagrammatic plan view of a particle analyzer embodying the invention.
Figure 8:
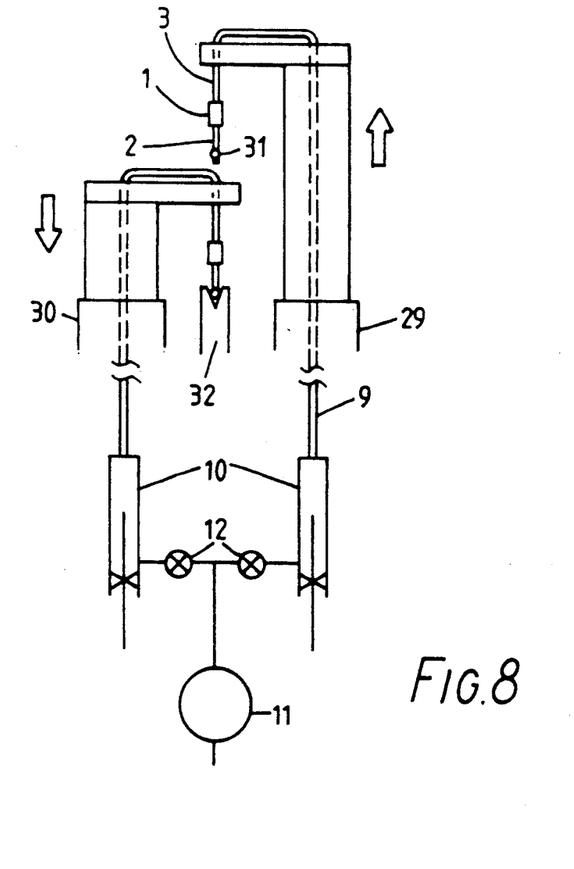
FIG. 8 is a diagrammatic side-view of the analyzer of FIG. 7.

The operation of the particle analyzer of FIG. 7 is as follows.

Each pipetter 29,30 sucks the reagent solution 4 from the reagent tank 5 and a particle suspension 6 from one of the sample vessels 7 in desired amounts. After the mixing and reaction is carried out sufficiently in the mixing chamber 1, by the repeated movement to and fro of the liquids into and out of the chamber 1 as described above, the mixed sample solution is supplied to the sheath flow cell 32. A tapering introduction port for the sample solution is disposed at the upper part of the sheath flow cell and communicates with the internal sample nozzle of the cell, and the O-ring 31 at the tip of the lower tube portion 2 is connected to it so that the sample solution can be pushed into the sheath flow cell 32 under a perfect seal. In the sheath flow cell 32, a sheath solution is supplied in synchronism with the sample solution to form the sheath flow. The laser beam is applied to the fine flow of particles so formed and each particle emits scattered light and/or fluorescence, which is condensed by the condensing lens 37 and converted to an output signal by the detector 38. Thus the particles can be counted and/or other analytical information about them can be obtained.

While the pipetter 30 is connected to the sheath flow cell 32, the other pipetter 29 has the residual sample solution for the previous measurement washed at the washing tank 34 and takes up and mixes the next sample for measurement. Since the measurement and the mixing are alternately conducted without interruption by use of the two pipetters, a large number of samples can be measured per unit time.

Next, another embodiment of the particle measuring apparatus will be explained with reference to FIGS. 9 and 10. The explanation will not be given for parts and operations already described. Here, pipette tubes 41,42,43,44,45,46 of six pipetters similar to those shown in FIG. 1 are fitted at six spaced positions on the outer periphery of a disc 40 with a gap of 60° between them. This disc 40 rotates by 60° steps clockwise (arrow 39), lowers for a predetermined time whenever it stops, then rises and thereafter repeats these operations. The means for moving the disc 40 are not shown. A rotary manifold valve is disposed at the centre on the lower surface of the disc 40 and consists of a rotor 47 which rotates with the disc 40 and a stator 48 which is always stationary and does not move. Flow paths exist through the rotor 47 and stator 48 at six positions in the circumferential direction with a gap of 60° between them. The flow paths of the rotor 47 are connected to the pipette tubes 41-46 respectively. The flow paths of the stator 48 in the circumferential direction are connected in sequence to a tube from a syringe 52 for reagent suction, to a tube from a syringe 51 for particle suspension suction, to two tubes from a mixing/reaction syringe 50, to a tube from a sample discharge syringe 49 and to a tube from the washing solution feed pump 11, respectively.

Figure 9:
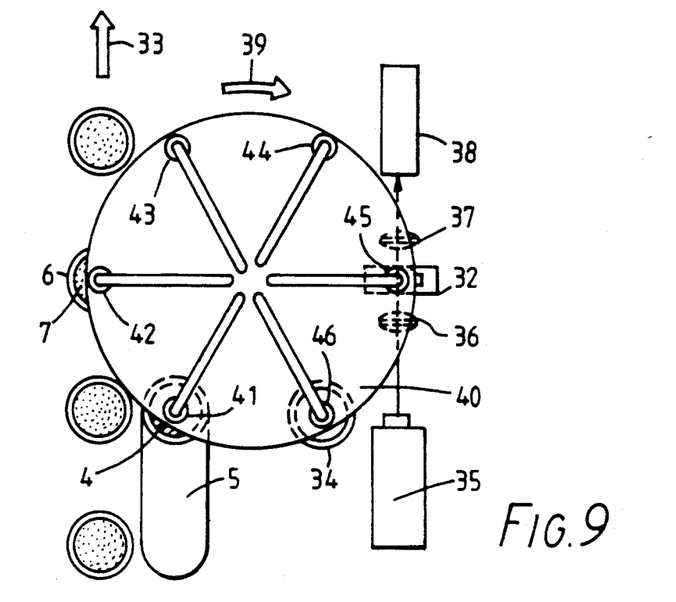
FIG. 9 is a general diagrammatic plan view of a second particle analyzer embodying the invention.
Figure 10:
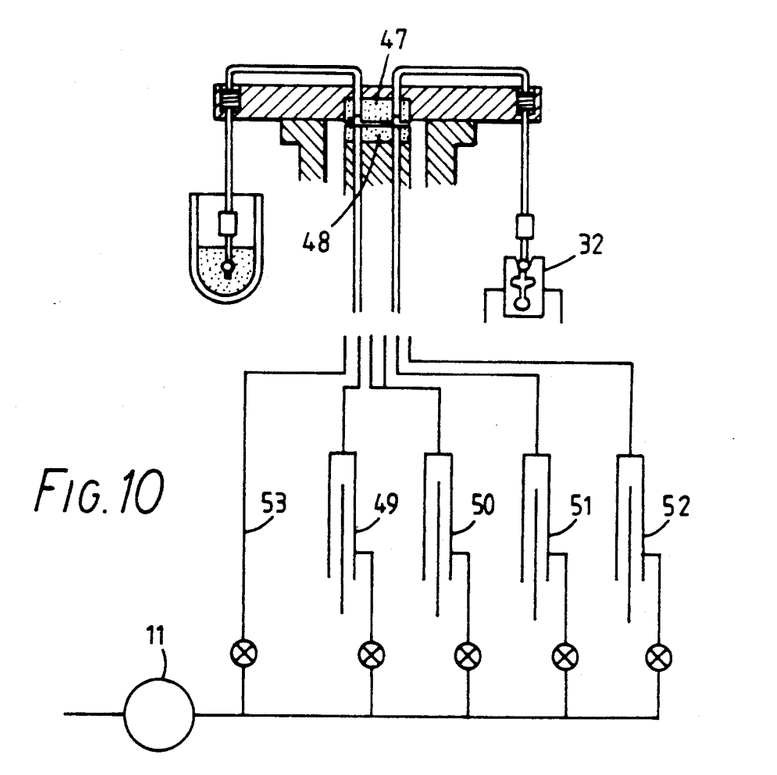
FIG. 10 is a diagrammatic vertical sectional view of the analyzer of FIG. 9.

The operation of the construction of FIGS. 9 and 10 is as follows.

FIG. 9 shows the state where the disc 40 has moved down. At this time the pipette tube 41 sucks a reagent solution from the reagent holding vessel 5, the pipette tube 42 sucks the particle suspension 7 from a sample holding vessel 6, the pipette tubes 43 and 44 perform mixing/reaction by repeated to and fro movement of liquid as described above under control of the mixing-/reaction syringe 50 and the pipette tube 45 supplies a mixed sample solution to the sheath flow cell 32. The pipette tube 46 is washed with the washing solution supplied thereto by the washing solution feed pump 11. When a predetermined time has passed at this state, the disc 40 rises and then rotates by 60°, lowering thereafter to repeat the operations described above. The flow paths of the rotor 47 and stator 48 are cut off during the rotation, and each syringe is opened at this time through a solenoid valve to receive the supply of the solution from the pump 11 as necessary to restore the initial syringe content.

As described above, when the disc 40 is operated, all the operations of the suction of the reagent solution, suction of the particle suspension, mixing/reaction, measurement and washing are carried out in each pipette tube during one rotation.

This embodiment provides the result that the sample processing capacity within a predetermined time can be improved remarkably. If, for example, a measurement time of 10 seconds and the driving time of 5 seconds for each movement of the disc 40 are assumed, 30 seconds is available for mixing and reaction. A handling rate of 240 samples/hour can be achieved.

Figure 11:
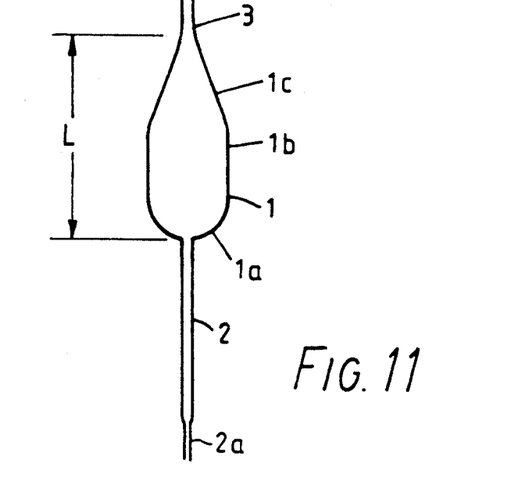
FIG. 11 is a side view of a pipette tube embodying the invention.

FIG. 11 illustrates a preferred shape of the pipette tube 1,2,3 of FIG. 1. In detail, the upper and lower tube portions 2,3 have an inside diameter of 0.7 mm, and the lower tube portion 2 has a narrower tip portion 2a of inside diameter 0.4 mm. A cylindrical portion 1b of the mixing chamber 1 has an inside diameter of 4 mm, while the radius of curvature of the bottom portion 1a is 2 mm. The overall length L of the chamber 1 is 12 mm and the length of the tapering portion 1c is 6 mm.

If desired, a heating jacket (not shown) may surround the mixing chamber 1, to maintain a desired temperature of the liquids being mixed.

Figures 12A, 12B:
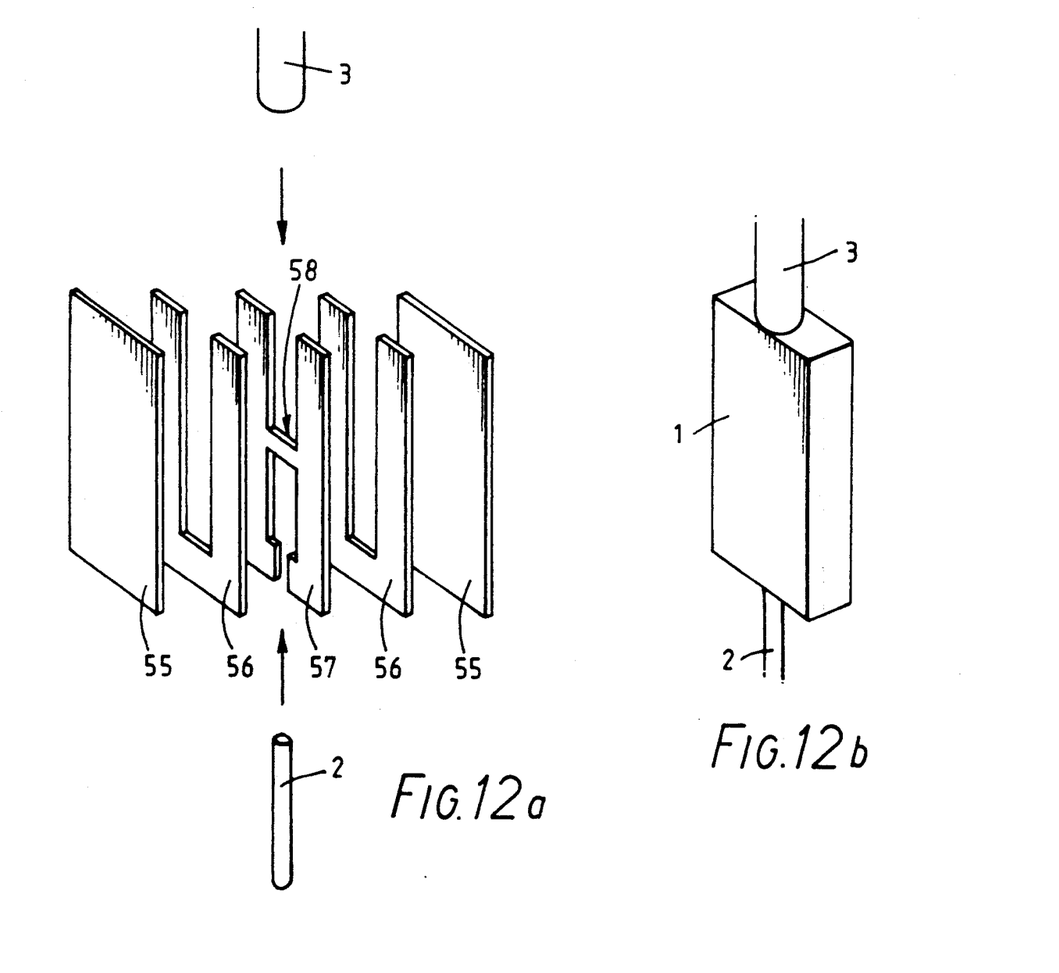

FIGS. 12a and 12b illustrate a further form of pipette tube 1,2,3 of the invention, made using thin layer technology. The mixing chamber 1 is formed from a plurality, in this case five, flat sheets 55,56,57. The outer sheets 55 are plain and define the side walls of the mixing chamber. The central sheets 56,57 have cutaway portions providing the mixing space and connections to the upper and lower tube portions 2,3. The shapes of the cutaway portions are such that there is a sharp transition in cross-sectional flow area on entry to the mixing chamber from the lower tube portion 2. The central sheet 57 includes a cross-bar 58 which extends across the flow path and constitutes an additional means of disturbing flow in the mixing chamber, increasing the mixing effect.

The pipetting and mixing apparatuses shown in FIG. 1 and FIGS. 7 to 10 are preferably controlled by programmed data processing means, e.g. a microcomputer. This is illustrated in FIG. 13 for the pipetter of FIG. 1 when the latter is employed to suck reagent and sample, mix them together by repeated reciporcation into and out of the mixing chamber 1 and discharge the mixed liquid to a flow cell, such as the sheath flow cell 32 of FIG. 7, for analysis. FIG. 13 identifies the three movements of the pipetter, i.e. (A) the stroke of the piston of the syringe pump 10, (B) the motion of the arm 8 to the four desired locations for respectively reagent pick-up, sample pick-up, flow cell for discharge and wash bottle for discharge of washing liquid and (C) the up and down motion of the pipette tube 1,2,3 at these locations. By the horizontal time scale, the coordination of these three movements is shown. Also given are the amounts of reagent and sample which are sucked and the preferred discharge rate at the flow cell. The repeated movement of the sample and reagent mixture partly in and out of the mixing chamber 1 to achieve the desired mixing of the sample is indicated by the section marked REPEAT. The preferred flow rate during this mixing step is about 5 µl/s. The number of repeated to and fro movements is preferably about 10.

What is claimed is:

1. Pipetter capable of mixing liquids, having
   (a) a pipetting tube having a first end for suction and discharge of liquid being pipetted and a second end,
   (b) actuating means connected to said second end of said tube for sucking liquid into and discharging liquid from said tube via said first end,
   (c) flow disturbance means in said tube spaced from said first end and adapted to cause longitudinal mixing of liquid in said tube when liquid is moved along said tube past said flow disturbance means in at least one direction,
   (d) control means for said actuating means adapted and arranged to effect mixing in said tube by causing said actuating means to move a liquid body repeatedly to and fro along said tube so that during each such movement at least a portion of said liquid body passes said flow disturbance means and said liquid body is not discharged from said first end of said tube; said control means being programmable and being programmed to cause said actuating means to effect said mixing.

2. Pipetter according to claim 1 wherein said control means is arranged to cause said actuating means to move said liquid body at least four times to and fro, to effect said mixing.

3. Pipetter according to claim 1 wherein said flow disturbance means is a mixing chamber having a lower end of a cross-sectional shape providing a sharp transition causing turbulent flow of liquid on entry into said chamber in the flow direction away from said first end of said tube.

4. Pipetter according to claim 4 wherein in vertical cross-section said lower end of said mixing chamber has an arcuate shape.

5. Pipetter according to claim 1 wherein said flow disturbance means comprises a plurality of vanes causing swirling of the liquid.

6. Pipetter according to claim 1, wherein said flow disturbance means comprises at least one element extending across the liquid flow path and causing eddying of the liquid.

7. Pipetter according to claim 1, wherein said flow disturbance means comprises a plurality of bends providing a serpentine region of the liquid flow path.

8. Pipetter according to claim 1, wherein said flow disturbance means comprises a wider liquid flow path region adjoining narrower liquid flow path regions wherein the liquid flow direction changes at the junction of at lest one of said narrower flow path regions to said wider flow path region.

9. A particle analyzer for analyzing suspended particles in a liquid sample, comprising
   (a) at least one sample container for said sample,
   (b) at least one container for a second liquid to be mixed with said sample prior to analysis thereof,
   (c) a sensor for analyzing particles in said sample after mixing with said second liquid,
   (d) a pipetter adapted and arranged for sucking a predetermined quantity of said sample from said sample container, mixing said sample with said second liquid to form a mixture thereof and discharging at least part of said mixture to said sensor, said pipetter comprising
      (i) a pipetting tube having a first end for suction and discharge of liquid being pipetted and a second end,
      (ii) actuating means connected to said second end of said tube for sucking liquid into and discharging liquid from said tube via said first end,
      (iii) flow disturbance means in said tube spaced from said first end and adapted to cause longitudinal mixing of liquid in said tube when liquid is moved past it in at least one direction, and
   (e) control means for said actuating means adapted and arranged to effect the formation of said mixture by causing said actuating means to move a liquid body constituted by said sample and said second liquid repeatedly to and fro along said tube so that during each such movement at least a portion of said liquid body passes said flow disturbance means and said liquid body is not discharged from said first end of said tube.

10. A particle analyzer according to claim 9 wherein said sensor comprises a cell connectable to said first end of said pipette tube for introduction of said mixture into said cell, said sensor including means for irradiating said particles in said cell and means for detecting radiation resulting from irradiation of said particles by said irradiating means.

11. Sample analyzing apparatus capable of simultaneous handling of a plurality of samples, comprising,
    (a) a plurality of sample containers for said samples,
    (b) at least one sensor for said samples,
    (c) a plurality of pipetters adapted and arranged for sucking said samples from said sample containers, forming mixtures of said samples with a second liquid and discharging said mixtures to said at least one sensor, each said pipetter comprising
       (i) a pipetting tube having a first end for suction and discharge of liquid being pipetted and a second end,
       (ii) flow disturbance means in said tube spaced from said first end and adapted to cause longitudinal mixing of liquid in said tube when liquid is moved past it in at least one direction, and
    (d) actuating means connectable to said second end of said pipetting tubes of said pipetters for sucking liquid into and discharging liquid from said tubes via said first ends thereof, and
    (e) control means for said actuating means adapted and arranged to achieve formation of each said mixture by causing said actuating means to move a liquid body constituted by the respective sample and said second liquid repeatedly to and fro along said tube of the pipetter so that during each such movement at least a portion of said liquid body passes said flow disturbance means while said liquid body is not discharged from said first end of the tube.

12. Sample analyzing apparatus according to claim 11 wherein said tubes of said pipetters are mounted on a rotatable carrier for sequential movement to a plurality of stations at which operations of the pipetters are performed.

* * * * *